(12) United States Patent
Gruenwald et al.

(10) Patent No.: US 6,694,801 B2
(45) Date of Patent: Feb. 24, 2004

(54) ELECTROCHEMICAL SENSOR ELEMENT

(75) Inventors: Werner Gruenwald, Gerlingen (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/088,611

(22) PCT Filed: Jun. 27, 2001

(86) PCT No.: PCT/DE01/02369
§ 371 (c)(1),
(2), (4) Date: Aug. 7, 2002

(87) PCT Pub. No.: WO02/06811
PCT Pub. Date: Jan. 24, 2002

(65) Prior Publication Data
US 2003/0029225 A1 Feb. 13, 2003

(30) Foreign Application Priority Data
Jul. 19, 2000 (DE) .......................... 100 35 036

(51) Int. Cl.⁷ ..................... G01N 7/00; G01N 27/26
(52) U.S. Cl. ............... 73/31.05; 73/23.32; 204/426; 204/427; 204/428
(58) Field of Search .................. 73/31.05, 31.06, 73/23.31, 23.32; 204/424–429

(56) References Cited

U.S. PATENT DOCUMENTS

| | | | | |
|---|---|---|---|---|
| 4,765,880 A | * | 8/1988 | Hayakawa et al. | 204/425 |
| 5,314,604 A | * | 5/1994 | Friese et al. | 204/410 |
| 5,505,837 A | * | 4/1996 | Friese et al. | 204/425 |
| 5,672,811 A | * | 9/1997 | Kato et al. | 73/31.05 |
| 5,686,654 A | * | 11/1997 | Friese et al. | 73/23.32 |
| 5,702,580 A | * | 12/1997 | Dietz et al. | 204/426 |
| 5,879,525 A | * | 3/1999 | Kato | 204/424 |
| 6,224,727 B1 | * | 5/2001 | Miyata et al. | 204/425 |
| 6,301,951 B1 | * | 10/2001 | Lenfers et al. | 73/23.31 |
| 6,325,906 B1 | * | 12/2001 | Kitanoya et al. | 204/425 |
| 6,346,178 B1 | * | 2/2002 | Lankheet | 204/424 |
| 6,348,140 B1 | * | 2/2002 | Matsubara et al. | 204/424 |
| 6,419,818 B2 | * | 7/2002 | Kato et al. | 205/781 |
| 6,517,702 B2 | * | 2/2003 | Stahl | 205/784.5 |

FOREIGN PATENT DOCUMENTS

| | | |
|---|---|---|
| DE | 196 47 144 | 5/1997 |
| EP | 580206 A1 * | 7/1993 |
| EP | 0 580 206 | 1/1994 |

* cited by examiner

Primary Examiner—Michael Cygan
(74) Attorney, Agent, or Firm—Kenyon & Kenyon

(57) ABSTRACT

An electrochemical sensor element for determining the oxygen concentration in exhaust gases of internal combustion engines is described. The sensor element has a pump cell, which has a pump electrode situated on a surface of the sensor element facing the gas mixture, and a measuring gas electrode situated in a measuring gas area, the gas mixture entering the measuring gas area through a diffusion resistor. In addition, the sensor element has a reference electrode situated in a reference gas area. Another diffusion resistor is provided between the measuring gas area and the reference gas area.

12 Claims, 6 Drawing Sheets

US 6,694,801 B2

ELECTROCHEMICAL SENSOR ELEMENT

FIELD OF THE INVENTION

The present invention relates to an electrochemical sensor element for determining the concentration of a gas component in a gas mixture, in particular for determining the oxygen concentration in exhaust gases of internal combustion engines.

BACKGROUND INFORMATION

An electrochemical sensor for determining oxygen concentration is described in German Published Patent Application No. 196 47 144, for example. The sensor elements described are used in gas detectors which are used to regulate the air/fuel ratio of combustion mixtures in automotive engines and as broadband lambda probes. A concentration cell is combined with an electrochemical pump cell in these sensor elements.

The concentration cell has a measurement electrode situated in a measuring gas area and a reference electrode situated in a reference gas area. The exhaust gas passes through a gas access orifice and a diffusion barrier to enter the measuring gas area. The reference gas area communicates with a reference atmosphere through an opening situated on the side of the sensor element facing away from the measuring gas area. The measuring gas area and the reference gas area are situated in the same layer plane of the sensor element, which is structured as a layered system and are separated by a gas-tight partition. A Nernst voltage develops between the measuring electrode and the reference electrode and can be used to determine the ratio of the oxygen partial pressure in the measuring gas area to the oxygen partial pressure in the reference gas area.

The pump cell has a first pump electrode situated in the measuring gas area and a second pump electrode situated on a surface of the sensor element facing the exhaust gas, and it pumps oxygen ions out of the measuring gas area into the exhaust gas, or conversely, out of the exhaust gas and into the measuring gas area. A pump voltage applied to the pump cell is regulated by an external circuit element, so that a predetermined oxygen partial pressure which corresponds to a certain Nernst voltage prevails in the measuring gas area. The pump voltage is selected so that the pump current flowing in the pump cell is limited by the diffusion rate of the oxygen molecules through the diffusion barrier, and the stream of oxygen molecules flowing through the diffusion barrier is proportional to the oxygen concentration in the exhaust gas, so the oxygen partial pressure of the exhaust gas can be determined from the pump current.

A disadvantage of the above-described sensor element is that the design of two gas spaces that are separated from one another in a gas-tight manner in one plane of the sensor element, namely the measuring gas area and the reference gas area, is complicated and difficult from the standpoint of the manufacturing technology.

SUMMARY OF THE INVENTION

The electrochemical sensor element according to the present invention has the advantage that the structure of the sensor element is greatly simplified by providing an additional diffusion resistor between the measuring gas area and the reference gas area. This achieves the result that it is not necessary to form a recess for the reference gas area separated from the measuring gas area in a gas-tight manner.

Since the gas component, generally oxygen, is pumped into the reference gas area by an external circuit element via the reference electrode, this achieves the result that a uniform partial pressure of the gas component prevails in the reference gas area, so that the partial pressure of the gas component in the measuring gas area may be determined with a good accuracy via the voltage difference (Nernst voltage) which develops between the measuring gas electrode and the reference electrode.

It is also advantageous that the reference gas area communicates with a gas space situated outside the sensor element only via the additional diffusion resistor. This prevents impurities from the reference gas atmosphere, for example, from entering the reference gas area, which could result in damage to the reference electrode and thus impair the sensor function.

The sensor design is greatly simplified further by the fact that the measuring gas area and/or the reference gas area is filled in at least some areas by a porous layer forming the diffusion resistor and/or the additional diffusion resistor.

Due to the fact that the reference gas area is situated in a channel-shaped area remote from the gas access orifice, this achieves the result that the concentration of the gas component in the reference gas area is influenced only slightly by fluctuations in the concentration of the gas component of the gas mixture.

Due to the fact that a measuring gas electrode and the reference electrode are situated in the same layer plane, this yields the manufacturing advantage that the measuring gas electrode and the reference electrode may be applied in a printing step.

DETAILED DESCRIPTION

Figure 1:
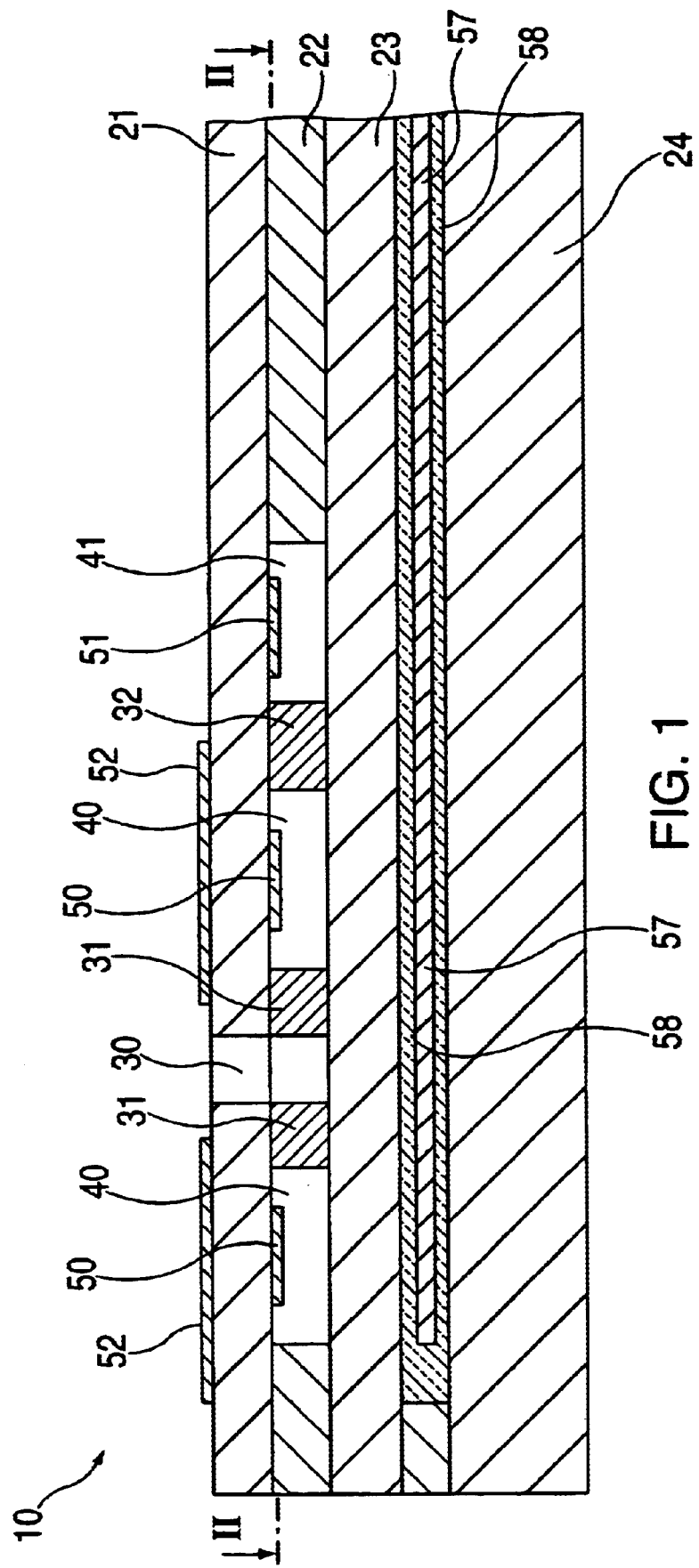
FIG. 1 shows a sectional diagram of a first embodiment of the sensor element according to the present invention along line I—I in FIG. 2.
Figure 2:
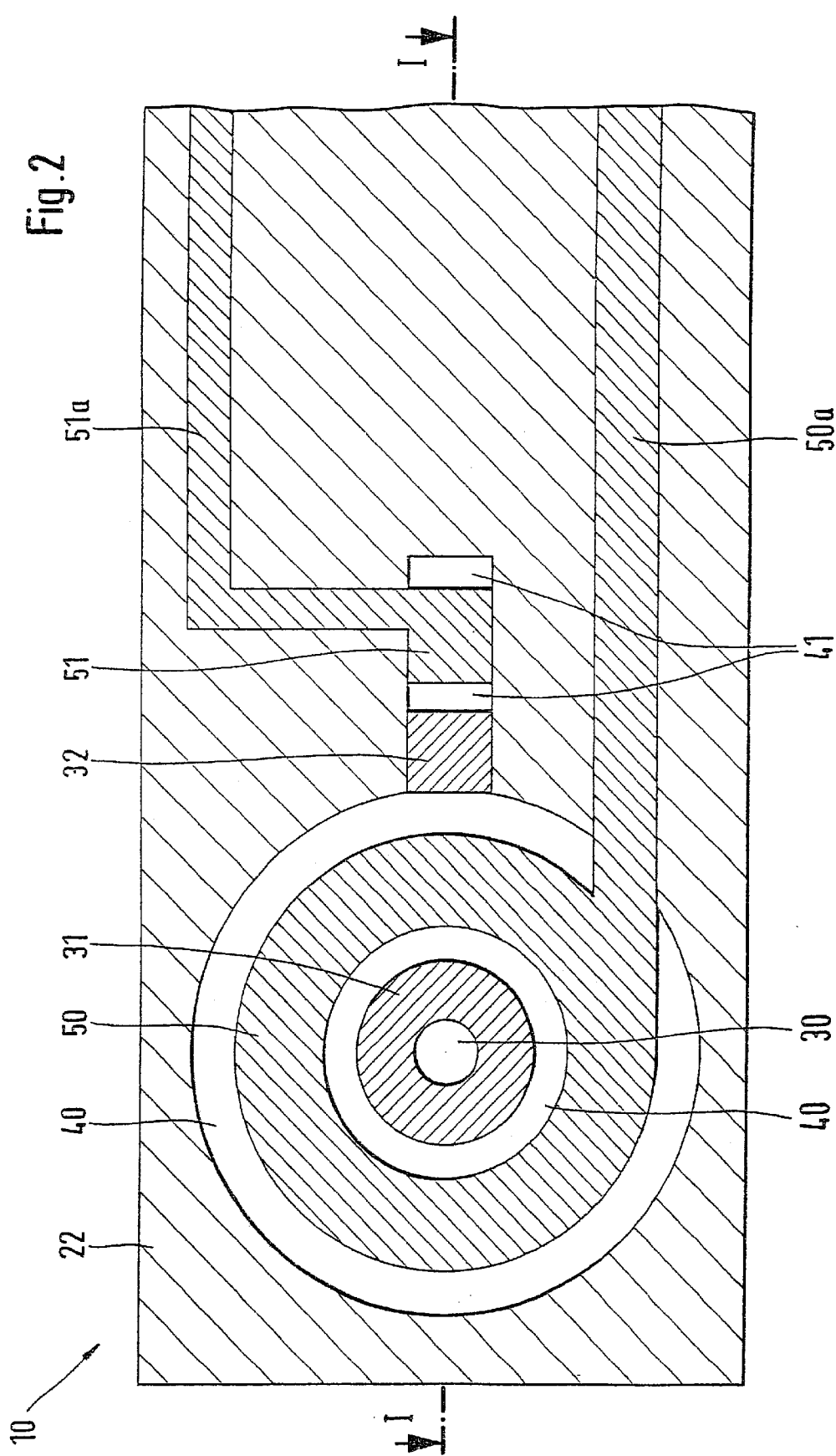
FIG. 2 shows a sectional-diagram of the first embodiment of the sensor element according to the present invention along line II—II in FIG. 1.

FIGS. 1 and 2 show as the first embodiment of the present invention a sensor element 10 of a broadband lambda probe designed as a layered system and having a first, second, third and fourth solid electrolyte layer 21, 22, 23, 24. A gas access orifice 30 is introduced into first and second solid electrolyte layers 21, 22. A recess containing a diffusion resistor 31, a measuring gas area 40, an additional diffusion resistor 32 and a reference gas area 41 is provided in second solid electrolyte layer 22. This recess is designed as a shallow cylindrical area, in the middle of which is provided gas access orifice 30 surrounded by hollow cylindrical diffusion resistor 31 and measuring gas area 40 which is also in the shape of a hollow cylinder, and a channel-shaped area which accommodates an additional diffusion resistor 32, directly adjacent to the cylindrical area, and reference gas area 41.

A ring-shaped measuring gas electrode 50 having a supply lead 50a is provided on first solid electrolyte layer 21 in measurement gap area 40, and a reference electrode 51 having a supply lead 51a is provided in reference gas area 41. A ring-shaped pump electrode 52 is applied to the outside surface of first solid electrolyte layer 21. Third and fourth solid electrolyte layers 23, 24 are adjacent to second solid electrolyte layer 22. A heating element 57 having a heating insulation 58 is provided between third and fourth solid electrolyte layers 23, 24.

Pump electrode 52 together with measuring gas electrode 50 forms a pump cell which pumps oxygen into or out of measuring gas area 40 through an external circuit element. The pump voltage applied to the pump cell through the external circuit element is regulated so that a predetermined oxygen partial pressure prevails in measuring gas area 40. An oxygen partial pressure of $\lambda=1$ is preferably set, i.e., the oxygen partial pressure corresponds to the stoichiometric air/fuel ratio.

The oxygen partial pressure prevailing in measuring gas area 40 is determined by a Nernst cell which is formed by measuring gas electrode 50 and reference electrode 51. A Nernst voltage produced by different oxygen partial pressures in measuring gas area 40 and in reference gas area 41 is measured using the Nernst cell and is used to regulate the pump voltage. This requires that a sufficiently constant oxygen partial pressure prevails in reference gas area 41. Therefore, a low pump current between measuring gas electrode 50 and reference electrode 51 or between pump electrode 52 and reference electrode 51 is produced by the external circuit element. Oxygen is pumped into reference gas area 41 by this pump current of 5 to 50 $\mu$A, for example. Depending on the oxygen partial pressure in the exhaust gas, the oxygen partial pressure in reference gas area 41 may vary, for example, in the range of 0.01 bar with rich exhaust gas to 0.3 bar with very lean exhaust gas. However, the effect of these fluctuations on the Nernst voltage is negligible.

The gas in reference gas area 41 may enter measuring gas area 40 through additional diffusion resistor 32. No additional connection to a gas space located outside the sensor element, such as the air atmosphere, is necessary. Because of the low pump current, the oxygen partial pressure in measuring gas area 40 is altered only to a negligible extent by venting of reference gas area 41 into measuring gas area 40.

According to one embodiment, reference electrode 51 is mounted on third solid electrolyte layer 23 in reference gas space 41.

Figure 3:
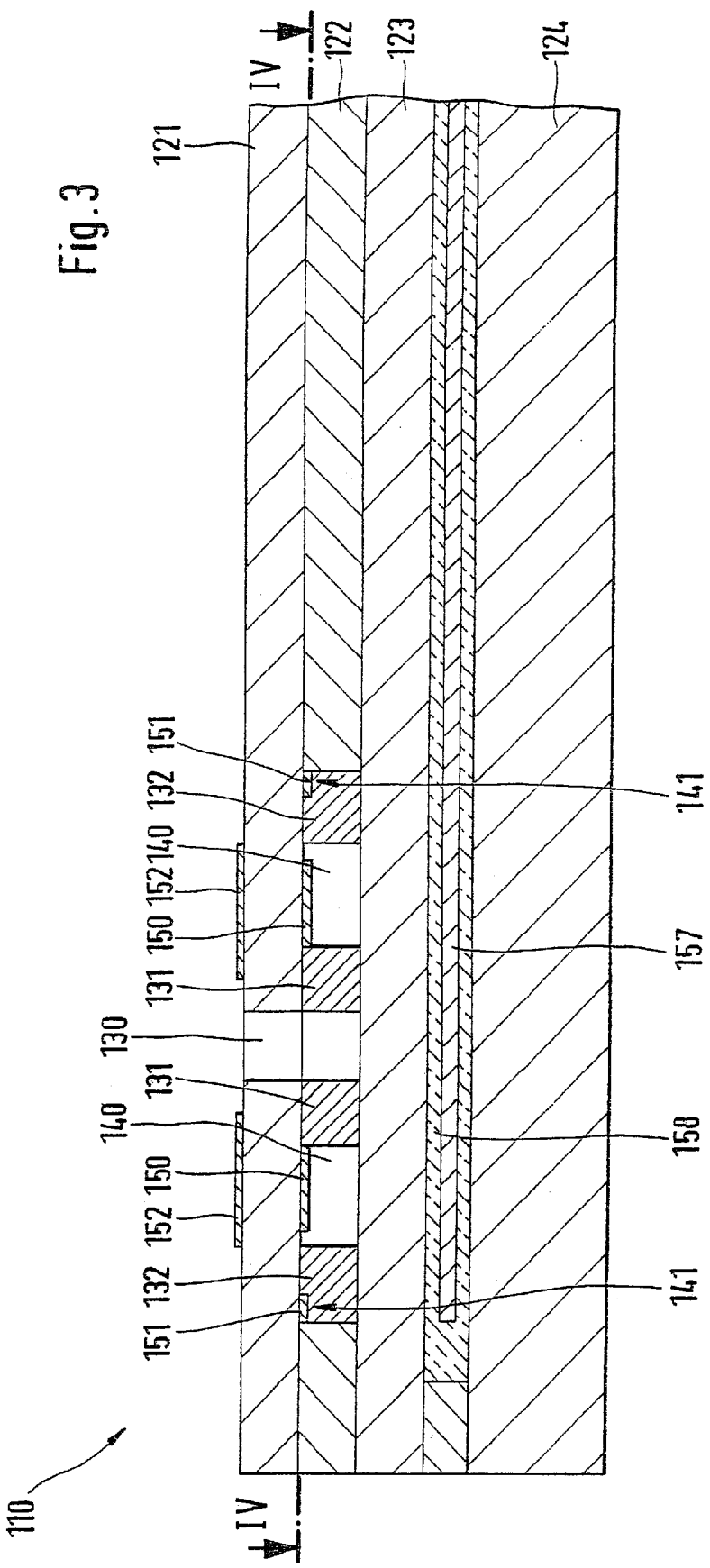
FIG. 3 shows a sectional diagram of a second embodiment of the sensor element according to the present invention along line III—III in FIG. 4.
Figure 4:
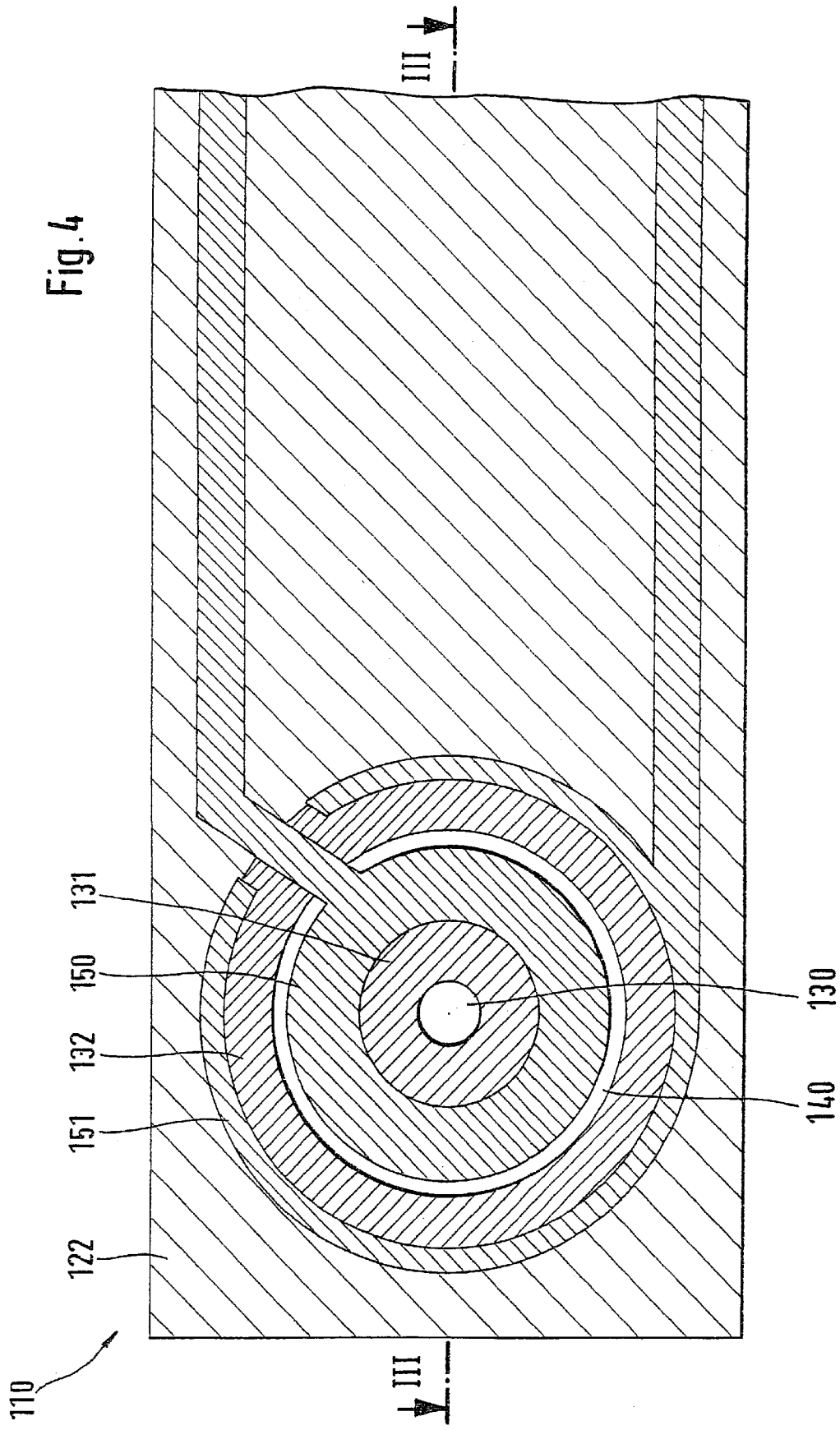
FIG. 4 shows a sectional diagram of the second embodiment of the sensor element according to the present invention along line VI—VI in FIG. 2.

FIGS. 3 and 4 show as the second embodiment of the present invention a sensor element 110 of a broadband lambda probe having a first and a second solid electrolyte layer 121, 122 into which is introduced a gas access orifice 130, and a third and fourth solid electrolyte layer 123, 124 between which is provided a heating element 157 having a heating insulation 158. Second solid electrolyte layer 122 has a recess containing a diffusion resistor 131, a measuring gas area 140 having a measuring gas electrode 150, an additional diffusion resistor 132, and a reference gas area 141 having a reference electrode 151. A pump electrode 152 is mounted on the outside surface of first solid electrolyte layer 121.

The second embodiment differs from the first embodiment in that additional diffusion resistor 132 and reference gas area 141 in the form of concentric hollow cylinders are also situated in a shallow cylindrical recess in addition to diffusion resistor 131 and measuring gas area 140. In addition, reference gas area 141 situated in the area of reference electrode 151 is filled completely by a porous material which forms additional diffusion resistor 132. Accordingly in this embodiment, reference gas area 141 is understood to refer to the area of the porous material adjacent to reference electrode 151.

According to one embodiment, the reference electrode in reference gas space 141 is applied to third solid electrolyte layer 123. It is also possible for the additional diffusion resistor not to cover reference electrode 151 at all or to cover it only in some areas.

Figure 5:
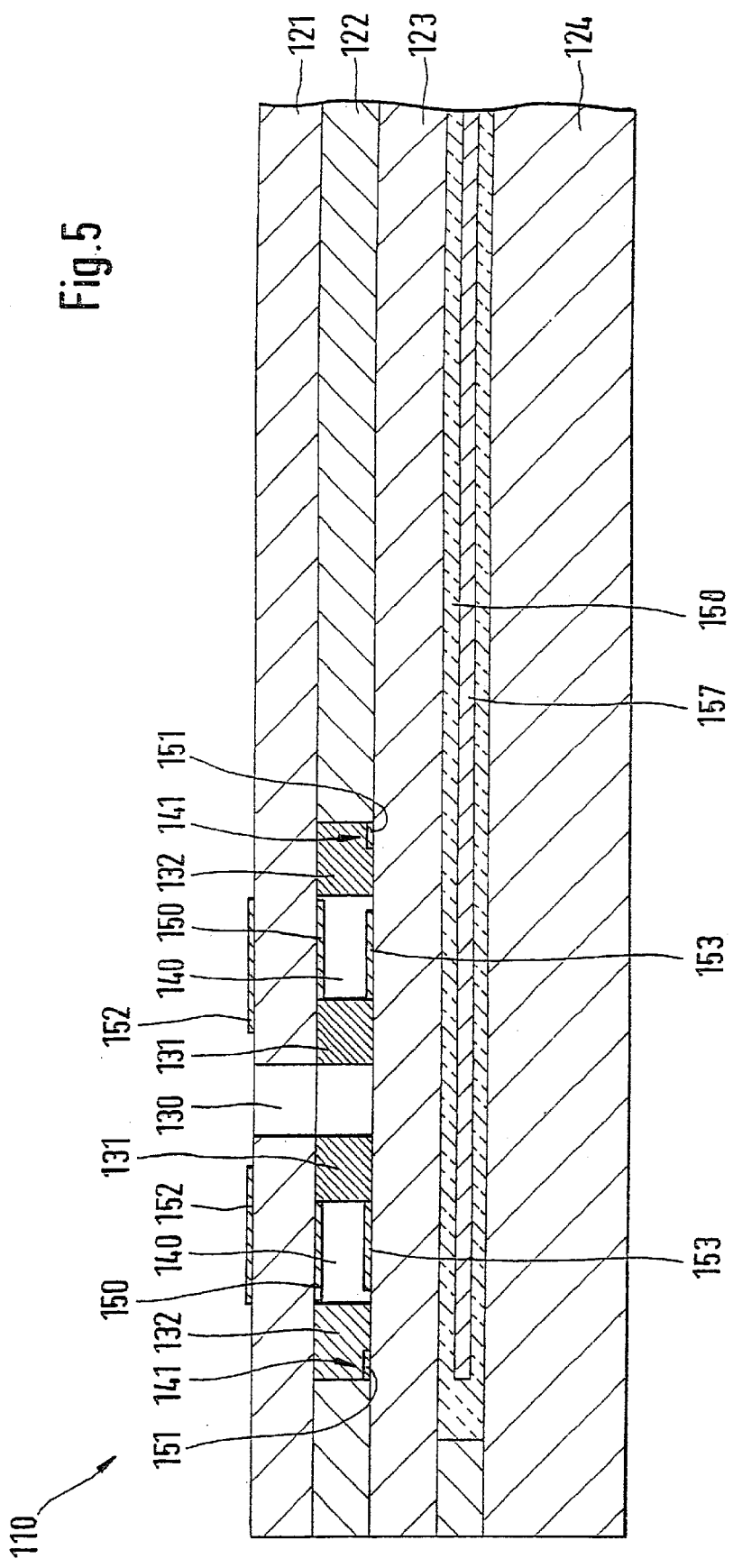
FIG. 5 shows a longitudinal section of additional embodiments of the sensor element according to the present invention.

FIG. 5 shows a third embodiment of the present invention which differs from the second embodiment in that reference electrode 151 in reference gas area 141 is applied to third solid electrolyte layer 123, and another measuring gas electrode 153 is applied to the third solid electrolyte layer and is opposite measuring gas electrode 150 in measuring gas area 140.

In this embodiment, additional measuring gas electrode 153 may be electrically connected to measuring gas electrode 150 in the supply lead area, for example. It is also possible for the Nernst cell to be formed by additional measuring gas electrode 153 and reference electrode 151 and for the pump cell to be formed by measuring gas electrode 150 and pump electrode 152. In this case, the pump current may flow between measuring gas electrode 150 and additional measuring gas electrode 153 and/or between pump electrode 152 and additional measuring gas electrode 153 to maintain the required oxygen partial pressure in reference gas area 141.

Figure 6:
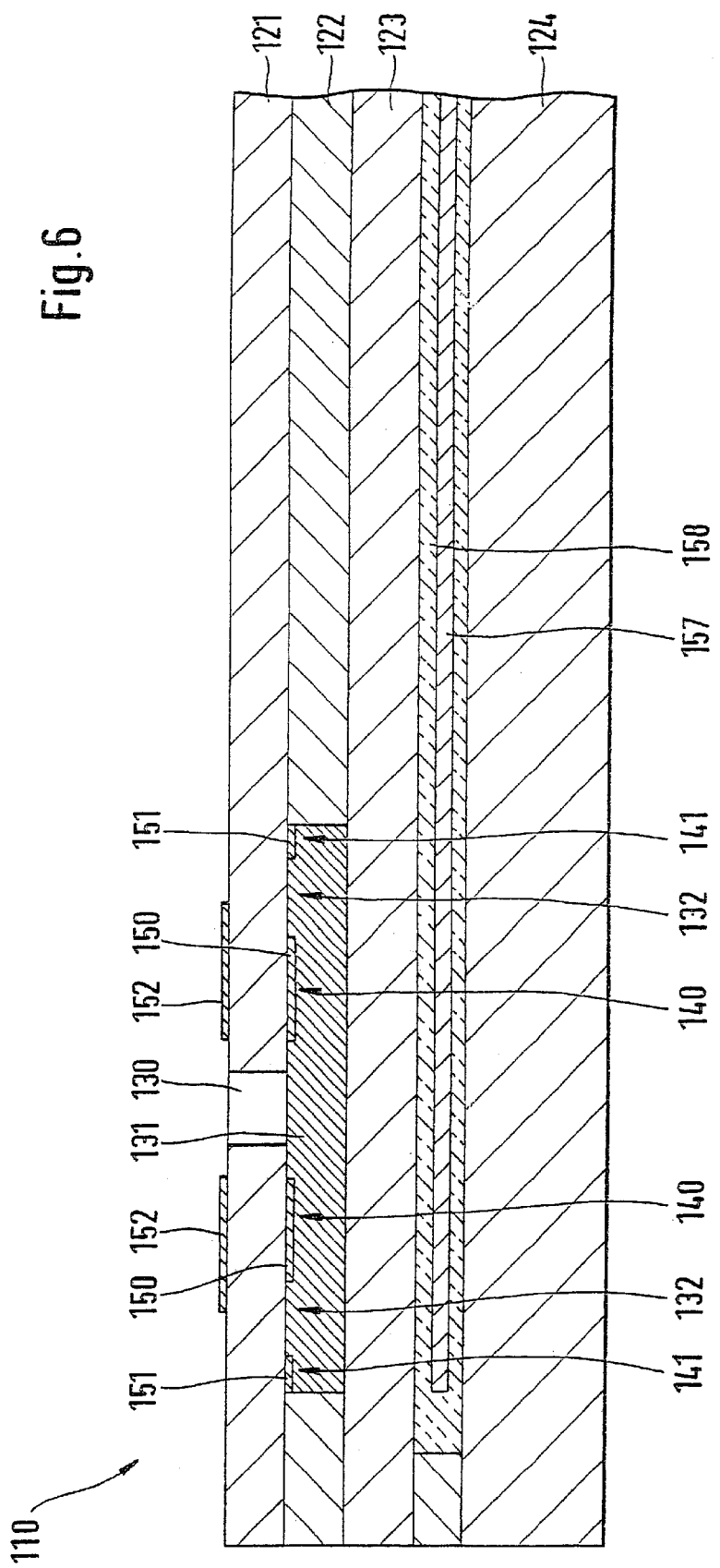
FIG. 6 shows another longitudinal section of additional embodiments of the sensor element according to the present invention.

FIG. 6 shows a fourth embodiment which differs from the second embodiment in that the recess in the second solid electrolyte layer containing diffusion resistor 131, measuring gas area 140, additional diffusion resistor 132, and reference gas area 141 is filled completely by a porous material. In this embodiment, measuring gas area 140 is understood to be the area of the porous material adjacent to measuring gas electrode 150, and reference gas area 141 is understood to be the area of the porous material adjacent to reference electrode 151. Diffusion resistor 131 is formed by the porous material situated between gas access orifice 130 and measuring gas electrode 150, and additional diffusion resistor 132 is formed by the porous material situated between measuring gas electrode 150 and reference electrode 151.

What is claimed is:
1. A sensor element for determining a concentration of a gas component in a gas mixture, comprising:
   a surface facing the gas mixture;
   a measuring gas area;
   a reference gas area;
   at least one pump cell including at least one pump electrode situated on the surface facing the gas mixture and including at least one measuring gas electrode situated in the measuring gas area;
   a diffusion resistor through which the gas mixture enters the measuring gas area;
   at least one reference electrode situated in the reference gas area; and
   an additional diffusion resistor provided between the measuring gas area and the reference gas area;
   wherein the gas component is pumped into the reference gas area by an external circuit element via the at least one pump electrode and the at least one reference electrode.

2. The sensor element of claim 1, wherein the sensor element is for determining a concentration of oxygen in an exhaust gas of an internal combustion engine.

3. The sensor element of claim 1, wherein the reference gas area is coupled to a gas space situated outside the sensor element only by the additional diffusion resistor.

4. The sensor element of claim 1, wherein the at least one measuring gas gas electrode includes a first measuring gas electrode and a second measuring gas electrode situated in the measuring gas area.

5. The sensor element of claim 4, wherein the second measuring gas electrode is electrically coupled to the first measuring gas electrode.

6. The sensor element of claims 4, wherein the gas component is pumped from the measuring gas area into the reference gas area by an external circuit element via at least one of:

a) the first measuring gas electrode and the at least one reference electrode; and b) the second measuring gas electrode and the at least one reference electrode.

7. The sensor element of claim 1, wherein the sensor element is arranged as a layered system, and the diffusion resistor, the measuring gas area, the additional diffusion resistor, and the reference gas area are situated at least predominantly in one layer plane of the sensor element.

8. The sensor element of 7, wherein the at least one measuring gas electrode and the at least one reference electrode are situated in a same layer plane of the sensor element.

9. The sensor element of 7, wherein the diffusion resistor, the measuring gas area, the additional diffusion resistor, and the reference gas area are situated in a cylindrical recess, and the at least one measuring gas electrode and the at least one reference electrode are annular in shape.

10. The sensor element of claim 7, wherein the diffusion resistor and the measuring gas area are situated in a cylindrical recess, the at least one measuring gas electrode is annular in shape, and the additional diffusion resistor and the reference gas area are situated in a further recess extending out of the measuring gas area in the form of a channel.

11. The sensor element of claim 1, wherein at least one of the diffusion resistor and the additional diffusion resistor include a porous layer.

12. The sensor element of claim 1, wherein at least one of the reference gas area and the measuring gas area includes at least a region of a porous layer, the at least one region of the porous layer forming at least one of the diffusion resistor and the additional diffusion resistor.

* * * * *